US009643142B2

(12) United States Patent
Pavlik

(10) Patent No.: US 9,643,142 B2
(45) Date of Patent: May 9, 2017

(54) PLUNGE-MIXING BAG ARRANGEMENT AND PLUNGE-MIXING SYSTEM

(71) Applicant: ADVANCED SCIENTIFICS, INC., Millersburg, PA (US)

(72) Inventor: Rudolf Pavlik, Millersburg, PA (US)

(73) Assignee: Advanced Scientifics, Inc., Millersburg, PA (US)

( * ) Notice: Subject to any disclaimer, the term of this patent is extended or adjusted under 35 U.S.C. 154(b) by 0 days.

(21) Appl. No.: 14/321,120

(22) Filed: Jul. 1, 2014

(65) Prior Publication Data

US 2016/0001242 A1  Jan. 7, 2016

(51) Int. Cl.
  *B01F 13/02* (2006.01)
  *B01F 11/00* (2006.01)
  *B01F 15/00* (2006.01)
  *B01F 3/04* (2006.01)
  *C12M 1/00* (2006.01)

(52) U.S. Cl.
  CPC ....... *B01F 13/0238* (2013.01); *B01F 3/04248* (2013.01); *B01F 11/0082* (2013.01); *B01F 15/0085* (2013.01); *C12M 23/14* (2013.01); *C12M 29/06* (2013.01)

(58) Field of Classification Search
  CPC .................................................. B01F 13/0238
  USPC ....... 261/81, 121.1, 123, 124; 366/102, 103, 366/107, 173.1, 173.2, 332
  See application file for complete search history.

(56) References Cited

U.S. PATENT DOCUMENTS

| | | | | |
|---|---|---|---|---|
| 438,998 | A * | 10/1890 | Glew ............................ | 502/401 |
| 4,079,008 | A * | 3/1978 | Neumann ........... | B01F 3/04099 210/194 |
| 4,189,243 | A * | 2/1980 | Black .................... | B01F 5/0659 366/336 |
| 6,007,237 | A * | 12/1999 | Latto ............................ | 366/315 |
| 6,416,215 | B1 | 7/2002 | Terentiev | |
| 6,494,613 | B2 | 12/2002 | Terentiev | |
| 6,660,224 | B2 * | 12/2003 | Lefebvre et al. ................. | 419/2 |
| 6,889,454 | B2 | 5/2005 | Chandaria | |
| 6,908,223 | B2 | 6/2005 | Bibbo et al. | |
| 6,923,567 | B2 | 8/2005 | Bibbo et al. | |
| 6,965,288 | B2 | 11/2005 | Terentiev | |
| 6,981,794 | B2 | 1/2006 | Bibbo et al. | |
| 7,086,778 | B2 | 8/2006 | Terentiev | |
| 7,267,479 | B2 | 9/2007 | Terentiev | |

(Continued)

FOREIGN PATENT DOCUMENTS

DE  10 2006 022 306 A1  11/2007
WO  2006/093572 A2  9/2006

OTHER PUBLICATIONS

International Search Report and Written Opinion dated Sep. 28, 2015, issued in PCT Application No. PCT/US2015/035158, filed Jun. 10, 2015.

*Primary Examiner* — Abbas Rashid
(74) *Attorney, Agent, or Firm* — Workman Nydegger

(57) ABSTRACT

A plunge-mixing bag arrangement includes a flexible mixing bag defining a mixing region, and a shaft extending from outside of the flexible mixing bag into the mixing region, the shaft comprising a sparger within the mixing region. The sparger comprises an interior channel and ports extending from the interior channel. The shaft is capable of axial movement within the bag to fracture gas bubbles being released from the interior channel through the ports. A plunge-mixing system includes a mechanism for raising and lowering the shaft.

18 Claims, 2 Drawing Sheets

(56) References Cited

U.S. PATENT DOCUMENTS

| | | |
|---|---|---|
| 7,357,567 B2 | 4/2008 | Terentiev |
| 7,384,027 B2 | 6/2008 | Terentiev et al. |
| 7,434,983 B2 | 10/2008 | Terentiev |
| 7,469,884 B2 | 12/2008 | Terentiev et al. |
| 7,481,572 B2 | 1/2009 | Terentiev |
| 7,516,648 B2 | 4/2009 | Terentiev |
| 7,695,186 B2 | 4/2010 | Terentiev |
| 7,762,716 B2 | 7/2010 | Terentiev et al. |
| 7,992,846 B2 | 8/2011 | Terentiev et al. |
| 8,123,188 B2 | 2/2012 | Banfield |
| 8,342,737 B2 | 1/2013 | Greller et al. |
| 8,455,242 B2 * | 6/2013 | Staheli et al. .............. 435/295.1 |
| 2001/0042929 A1* | 11/2001 | Rexford et al. ............ 261/122.1 |
| 2005/0161477 A1* | 7/2005 | Strecker et al. ............... 222/504 |
| 2006/0148267 A1* | 7/2006 | Hansen et al. ................. 438/745 |
| 2006/0196501 A1* | 9/2006 | Bibbo et al. .............. 128/200.23 |
| 2006/0270036 A1* | 11/2006 | Goodwin et al. ............. 435/395 |
| 2010/0197003 A1 | 8/2010 | Terentiev et al. |
| 2011/0207218 A1* | 8/2011 | Staheli et al. ................. 435/394 |
| 2013/0101982 A1* | 4/2013 | Goodwin et al. ................. 435/3 |
| 2013/0150268 A1* | 6/2013 | Oldham ................... C09K 8/62<br>507/215 |

* cited by examiner

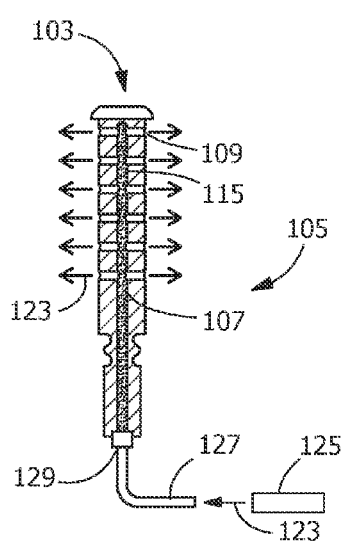
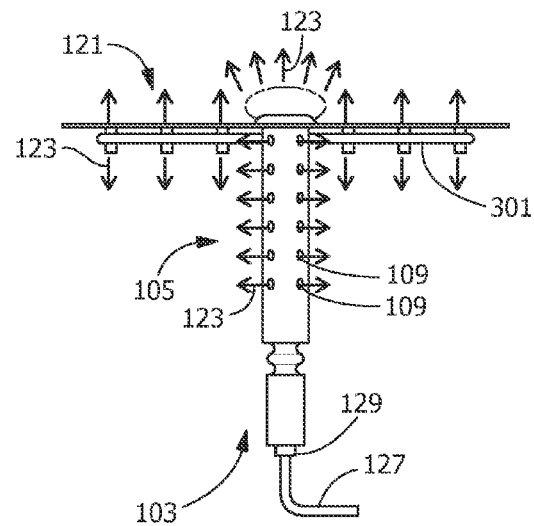
FIG. 2
FIG. 3
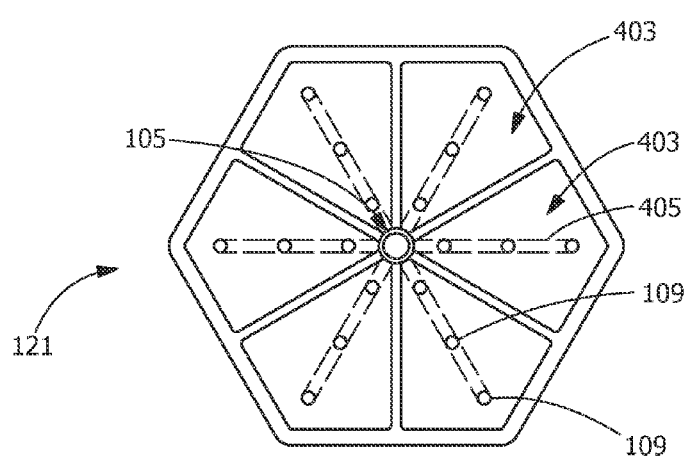
FIG. 4

PLUNGE-MIXING BAG ARRANGEMENT AND PLUNGE-MIXING SYSTEM

FIELD OF THE INVENTION

The present invention is directed to mixing devices, systems and processes. More particularly, the present invention is directed to plunge-mixing.

BACKGROUND OF THE INVENTION

Many pharmaceutical solutions and suspensions on an industrial scale rely upon highly-controlled, thorough mixing to achieve desired distribution of ingredients in a final product. Agitator tanks are frequently used to complete the mixing processes. Also mechanical stirrers or impellers are also frequently used. Typically, the mechanical stirrers or impellers are lowered into the fluid through an opening in the top of the vessel and rotated by an external motor to create a mixing action.

Substantial operational procedures are employed to make sure that such techniques do not suffer from drawbacks of contamination and/or leakage during the mixing. Otherwise, the rod carrying the mixing blades or impeller introduced into the vessel would introduce bacteria or other contaminants, which would lead to degradation of the product. Corresponding efforts are employed in applications involving hazardous or toxic fluids, or suspensions of pathogenic organisms.

Consumable bags have been used to further augment such issues. Some known systems rely upon magnetically-driven impellers and/or immobile spurge discs contained within the consumable bags. Further improvements to the design, efficiency and operation of such consumable bags and the features operating in conjunction with such consumable bags continue to be a desirable goal.

A plunge-mixing bag arrangement and a plunge-mixing system that show one or more improvements in comparison to the prior art would be desirable in the art.

BRIEF DESCRIPTION OF THE INVENTION

In an embodiment, a plunge-mixing bag arrangement includes a flexible mixing bag defining a mixing region, and a shaft extending from outside of the flexible mixing bag into the mixing region, the shaft comprising a sparger within the mixing region. The sparger comprises an interior channel and ports extending from the interior channel. The shaft is capable of axial movement within the bag to fracture gas bubbles being released from the interior channel through the ports.

In another embodiment, a plunge-mixing bag arrangement includes a flexible mixing bag defining a mixing region, a shaft extending from outside of the flexible mixing bag into the mixing region, the shaft comprising a sparger within the mixing region, the sparger comprising an interior channel and ports extending from the interior channel, a porous material between the interior channel and the ports, and a mixing head positioned opposite from where the sparger extends from the outside into the mixing region. The shaft is capable of axial movement within the bag to fracture gas bubbles being released from the interior channel through the ports. The interior channel terminates prior to reaching the mixing head.

In another embodiment, a plunge-mixing system includes a mechanism for raising and lowering, a shaft extending upward from the mechanism and from outside of a flexible mixing bag into a mixing region defined by the flexible mixing bag, the shaft comprising a sparger within the mixing region, the sparger comprising an interior channel and ports extending from the interior channel, and the flexible mixing bag. The shaft is capable of axial movement within the bag to fracture gas bubbles being released from the interior channel through the ports.

In another embodiment, a plunge-mixing process includes raising and lowering a shaft extending upward from a mechanism in a plunge-mixing system and from outside of a flexible mixing bag into a mixing region defined by the flexible mixing bag, releasing gas from a sparger within the mixing region and part of the shaft, and fracturing gas bubbles being released from the interior channel through the ports.

In another embodiment, a fabrication process includes positioning a shaft having an interior channel, forming holes to extend from the interior channel through the shaft to an exterior surface of the shaft, and positioning a porous material between the interior channel and the exterior surface.

In another embodiment, a fabrication process includes positioning a shaft having an interior channel and ports extending from the interior channel through the shaft to an exterior surface of the shaft, and positioning a porous material between the interior channel and the exterior surface.

Other features and advantages of the present invention will be apparent from the following more detailed description, taken in conjunction with the accompanying drawings which illustrate, by way of example, the principles of the invention.

BRIEF DESCRIPTION OF THE DRAWINGS

FIG. 2 is a perspective view of a shaft having a sparger, according to an embodiment of the disclosure.

FIG. 3 is a perspective view of a shaft having a sparger, according to an embodiment of the disclosure.

FIG. 4 is a top view of a mixing head for connection with a sparger, according to an embodiment of the disclosure.

Wherever possible, the same reference numbers will be used throughout the drawings to represent the same parts.

DETAILED DESCRIPTION OF THE INVENTION

Figure 1:
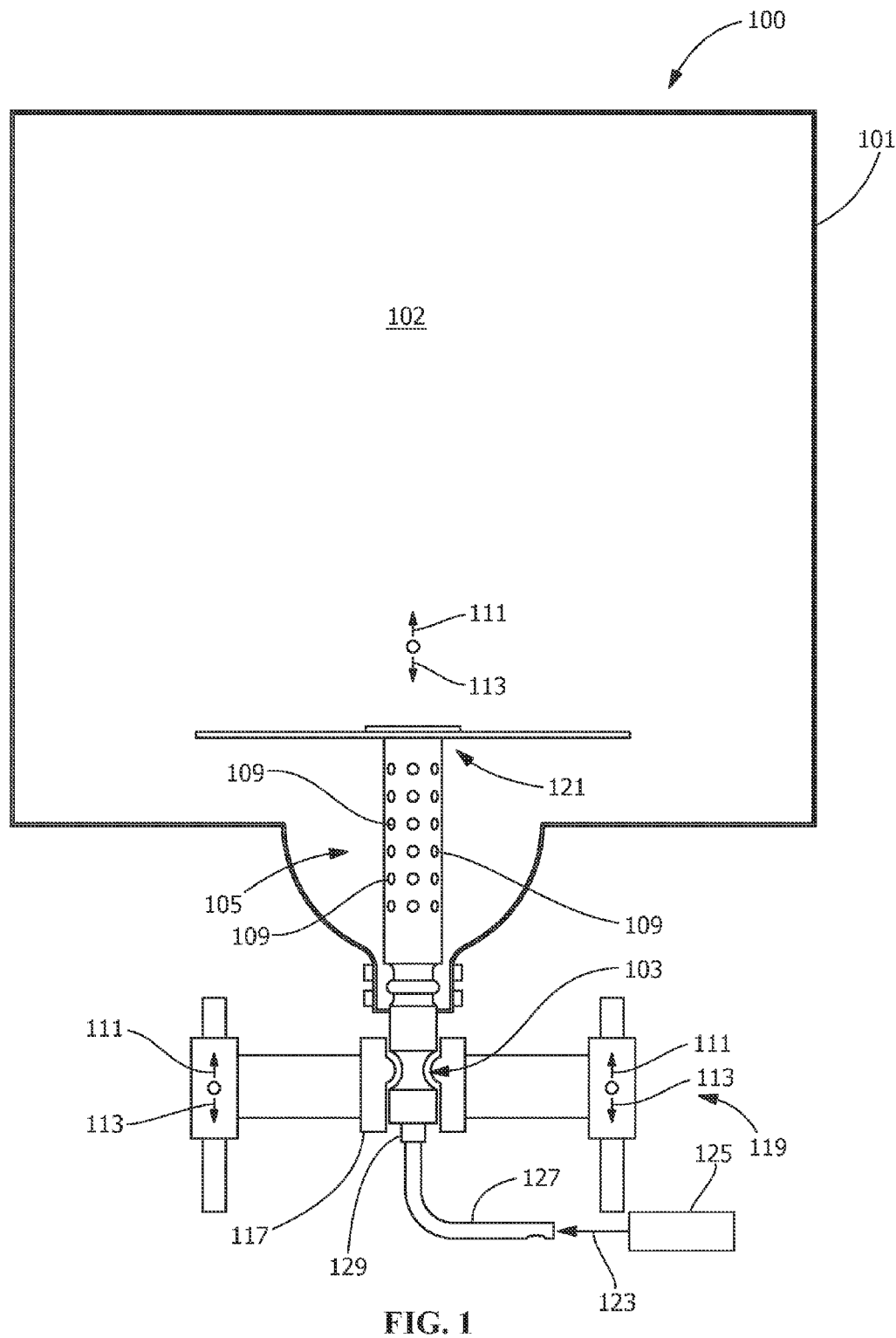
FIG. 1 is a schematic view of an embodiment of a plunge-mixing bag arrangement positioned within an embodiment of a plunge-mixing system.

Provided is a plunge-mixing bag arrangement and a plunge-mixing system capable of use in or with the systems describe in detail in U.S. Pat. No. 6,923,567, which issued on Aug. 2, 2005, and is hereby incorporated by specific reference in its entirety. Embodiments of the present disclosure, for example, in comparison to concepts failing to include one or more of the features disclosed herein, permit increases in operational efficiency in the mixing of pharmaceutical materials, fermentation materials, bioreactor materials, permit greater control of bubble size and/or frequency from gas introduced during mixing, permit greater operational flexibility and control during mixing, permit the fracture and/or reduction in size of bubbles released into a mixing region, reduce or eliminate damage to mixing materials (such as cells) through increased uniformity of distribution of bubbles, permit bubbles to be released at a lower velocity, permit other advantages and benefits that will be apparent from the disclosure, or a combination thereof.

Referring to FIG. 1, in one embodiment, a plunge-mixing bag arrangement 100 includes a flexible mixing bag 101 defining a mixing region 102, and a shaft 103 extending from outside of the flexible mixing bag 101 into the mixing region 102. The shaft 103 is integrally secured to the flexible mixing bag 101 by a rolling diaphragm. The flexible mixing bag 101 is any suitable material capable of being used for mixing of pharmaceutical materials, fermentation materials, bioreactor materials, or a combination thereof. In one embodiment, the flexible mixing bag 101 includes a polymeric material meeting the sterilization requirements of the United States Food and Drug Agency (FDA) and a USP Class VI materials.

The shaft 103 includes a sparger 105 within the mixing region 102. The sparger 105 includes an interior channel 107 and ports 109 extending from the interior channel 107, as shown in FIG. 2. The sparger 105 and/or the shaft 103 is/are capable of axial movement within the flexible mixing bag 101 to constrict and/or fracture gas bubbles (for example, air bubbles, nitrogen bubbles, $CO_2$ bubbles, $O_2$ bubbles, inert gas bubbles, or other suitable gas bubbles) provided by a gas 123 from a gas supply source 125 connected by a flexible hose 127 via a hose connector 129. The gas bubbles are released from the interior channel 107 through the ports 109 and/or from below the sparger 105. As used herein, the phrase "axial movement" refers to bilateral movement parallel to or substantially parallel to the shaft 103. For example, in one embodiment, the axial movement is along an upward direction 111 and a downward direction 113. As used herein, directional terms are intended to correspond with gravity being consistent with, parallel to, or substantially parallel to the downward direction 113 of the axial movement shown in FIG. 1. In one embodiment, the axial movement is induced by a drive capable of variable speed and stroke.

The plunge-mixing bag arrangement 100 is capable of being positioned in a plunge-mixing system 119. The plunge-mixing system 119 is configured for the axial movement of the sparger 105 by having a mechanism 117 or drive for raising and lowering the shaft 103. The mechanism 117 is any device capable of repeated movement and controlled movement. The shaft 103 extends upward from the plunge-mixing system 119 and the mechanism 117 for the raising and the lowering. The plunge-mixing system 119 is capable of including any other features for plunge-mixing processes.

The shaft 103 includes features for controlling the release, the fracture, and/or the constriction of gas through the sparger 105 during the axial movement. The sparger 105 includes or is devoid of a porous material 115 (see FIG. 2) between the interior channel 107 and the ports 109. The porous material 115 limits the flow of the air bubbles based upon size (for example, by having a smaller surface area than the ports 109) and by speed (for example, by having a higher coefficient of friction than the materials of the sparger 105 and/or the ports 109), for example, by creating a constricted and/or tortuous path for the gas. In one embodiment, the ports 109 close on the down-stroke of the sparger 105 and the air bubbles are distributed and forced down and between the sparger 105 and the inner side of the flexible mixing bag 101, thereby breaking the air bubbles into being of a smaller size and evenly distributed. In one embodiment, flow through the ports 109 is sequentially restricted or precluded, for example, by valves, such as, one-way valves.

The porous material 115 includes properties for selected applications, such as, being hydrophobic to prevent, reduce, or eliminate fluid from travelling from the mixing region 102 into the interior channel 107. The porous material 115 is any suitable material compatible with the sparger 105 and capable of operation during plunge-mixing. Suitable materials include, but are not limited to, a porous polymer (such as, those available from Porex Corporation, Atlanta, Ga.), a foam, a metallic foam, charcoal, pumice, or a combination thereof. The porous material 115 is permanently adhered or secured to the sparger 105 or is removable and/or replaceable.

The sparger 105 includes any suitable geometry and features for the plunge-mixing process. Although the embodiments of the sparger 105 shown in FIGS. 1-4 all have a cylindrical tube geometry, other suitable geometries include, but are not limited to, a generally-cylindrical tube, a square tube, a generally-square tube, a generally-triangular tube, a triangular tube, a generally-oval tube, an oval tube, a generally-rectangular tube, and a rectangular tube. As used herein, the term "generally" is intended to cover geometries that resemble a specified geometry but are not technically the specified geometry, for example, by having rounded edges/corners instead of perpendicular edges/corners and/or by having imprecise dimensions.

The sparger 105 includes a polymeric material, a metal material, a metallic material, another suitable material, or a combination thereof. The ports 109 within the sparger 105 are formed within the sparger 105 based upon the material and/or based upon desired properties. For example, in some embodiments, the ports 109 are formed by drilling holes perpendicular, at an angle above perpendicular, or below perpendicular from the interior channel 107. Alternatively, in some embodiments, the sparger 105 is molded to have the ports 109 positioned perpendicular, at an angle above perpendicular, or below perpendicular from the interior channel 107. The ports 109 are arranged concentrically around the sparger 105, with greater frequency on certain portions of the sparger 105 (for example, proximal or distal from the plunge-mixing system 119), with equal frequency throughout the sparger 105, extending from the interior channel 107 in more than a select number of directions (for example, at least three directions, at least four directions, at least five directions, at least six directions, etc.), increasing or decreasing in size as the ports 109 extend from the interior channel 107, in other suitable arrangements, or a combination thereof.

The gas provided from the interior channel 107 and released through the ports 109 is provided from the plunge-mixing system 119. For example, in one embodiment, the interior channel 107, which is enclosed by the shaft 103, extends from beyond the sparger 105 portion of the shaft 103 into the portion of the shaft 103 proximal to the plunge-mixing system 119. Gas is selectively provided to the interior channel 107 during the plunge-mixing process, for example, at a select pressure (for example, above 0 pounds and below 100 pounds) and/or a select temperature (for example, above 0° C. and below 80° C.).

In one embodiment, the interior channel 107 extends in a linear or substantially linear direction and terminates within the shaft 103 proximal to the end of the sparger 105 where a mixing head 121 is positioned. Alternatively, the interior channel 107 extends into the mixing head 121 and a plurality of the ports 109 are positioned in the mixing head 121, for example, around the mixing head 121 and/or below the mixing head 121, which is believed to result in additional mixing uniformity and/or distribution of bubbles. The mixing head 121 includes any suitable mixing apparatus, such as, a substantially planar circle 201 as shown in FIG. 2, an oval plunger and/or one or more horizontal channels 301 in the mixing head 121 as shown in FIG. 3, the mixing head 121 being hexagonal with flaps 403 (for example, silicone) separated by a flap hinge 405 having the ports 109 as shown in FIG. 4, a disc, a rot, a ring, and/or any other suitable features.

While the invention has been described with reference to one or more embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A plunge-mixing bag arrangement, comprising:
a flexible mixing bag defining a mixing region;
an elongated shaft having a first end disposed outside of the flexible mixing bag and an opposing second end disposed within the mixing region, the shaft comprising a sparger, the sparger comprising an interior channel extending through the shaft from the first end disposed outside of the flexible mixing bag to the opposing second end disposed within the mixing region and a plurality of ports extending from the interior channel at locations upstream from the second end to an exterior surface of the shaft within the mixing region;
a porous material disposed within the interior channel of the shaft so as to continuously extend from the first end disposed outside of the flexible mixing bag to the opposing second end disposed within the mixing region so that when a gas passes through the sparger, the gas passes through the porous material, the porous material forming a constricted flow path for the gas; and
a mixing head connected to the shaft opposite from where the shaft extends from the outside into the mixing region;
wherein the shaft is capable of axial movement within the bag to fracture gas bubbles being released from the interior channel through the ports.

2. The plunge-mixing bag arrangement of claim 1, wherein the porous material is hydrophobic, thereby preventing fluid from travelling from the mixing region into the interior channel.

3. The plunge-mixing bag arrangement of claim 1, wherein the porous material comprises a porous polymer.

4. The plunge-mixing bag arrangement of claim 1, wherein the porous material comprises a foam.

5. The plunge-mixing bag arrangement of claim 1, wherein the porous material comprises a metallic foam.

6. The plunge-mixing bag arrangement of claim 1, wherein the porous material comprises charcoal.

7. The plunge-mixing bag arrangement of claim 1, wherein the porous material comprises pumice.

8. The plunge-mixing bag arrangement of claim 1, wherein the plurality of ports are positioned to extend from the interior channel to at least four different directions on the shaft.

9. The plunge-mixing bag arrangement of claim 1, wherein the mixing head is a substantially planar circle with a diameter of at least twice a width of the shaft.

10. The plunge-mixing bag arrangement of claim 1, wherein the shaft has a geometry of a cylindrical tube.

11. The plunge-mixing bag arrangement of claim 1, wherein the bag arrangement is positioned within a plunge-mixing system and the shaft extends upward from a mechanism of the plunge-mixing system for raising and lowering the shaft.

12. The plunge-mixing bag arrangement of claim 1, wherein the shaft is formed of a polymeric material.

13. The plunge-mixing bag arrangement of claim 1, wherein the shaft is formed of a metal material.

14. The plunge-mixing bag arrangement of claim 1, wherein each of the plurality of ports extend at an angle above or below perpendicular to the interior channel of the shaft.

15. The plunge-mixing bag arrangement of claim 1, wherein some of the plurality of ports are disposed at a greater frequency at certain portions along the length of the shaft than others of the plurality of ports.

16. The plunge-mixing bag arrangement of claim 1, wherein the plurality of ports increase or decrease in size as the ports extend from the interior channel to the exterior surface of the shaft.

17. The plunge-mixing bag arrangement of claim 1, wherein the porous material is not disposed within the plurality of ports.

18. The plunge-mixing bag arrangement of claim 1, wherein the porous material is removable from the shaft and replaceable.

* * * * *